United States Patent
Bani-Hashemi

(10) Patent No.: US 7,016,522 B2
(45) Date of Patent: Mar. 21, 2006

(54) PATIENT POSITIONING BY VIDEO IMAGING

(75) Inventor: Ali Bani-Hashemi, Walnut Creek, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 730 days.

(21) Appl. No.: 10/051,588

(22) Filed: Jan. 15, 2002

(65) Prior Publication Data
US 2003/0133602 A1   Jul. 17, 2003

(51) Int. Cl.
G06K 900/00   (2006.01)

(52) U.S. Cl. .................. 382/131; 382/132; 250/363.04; 600/425; 600/407

(58) Field of Classification Search .............. 382/128, 382/129, 130, 131, 132, 133, 134; 600/425, 600/409, 407, 205, 130; 378/4, 8, 20, 21–27, 378/65, 150, 205–207, 68–69; 250/455, 250/378, 363.04, 363.05, 582–583; 324/248, 324/261
See application file for complete search history.

(56) References Cited

U.S. PATENT DOCUMENTS

| | | | |
|---|---|---|---|
| 4,907,252 A | 3/1990 | Aichinger et al. | |
| 5,315,630 A | 5/1994 | Sturm et al. | |
| 5,317,616 A | 5/1994 | Swerdloff | |
| 5,351,280 A | 9/1994 | Swerdloff | |
| 5,394,452 A | 2/1995 | Swerdloff | |
| 5,442,675 A | 8/1995 | Swerdloff | |
| 5,446,548 A | 8/1995 | Gerig et al. | |
| 5,528,650 A | 6/1996 | Swerdloff | |
| 5,548,627 A | 8/1996 | Swerdloff | |
| 5,625,663 A | 4/1997 | Swerdloff | |
| 5,661,773 A | 8/1997 | Swerdloff | |
| 5,673,300 A * | 9/1997 | Reckwerdt et al. | 378/65 |
| 5,724,400 A | 3/1998 | Swerdloff | |
| 5,954,647 A * | 9/1999 | Bova et al. | 600/407 |
| 6,385,286 B1 * | 5/2002 | Fitchard et al. | 378/65 |
| 6,865,254 B1 * | 3/2005 | Nafstadius | 378/65 |
| 2003/0112922 A1 * | 6/2003 | Burdette et al. | 378/65 |
| 2003/0206614 A1 * | 11/2003 | Kendrick et al. | 378/205 |
| 2004/0138556 A1 * | 7/2004 | Cosman | 600/424 |

FOREIGN PATENT DOCUMENTS

| | | |
|---|---|---|
| EP | 0 812 605 A2 | 12/1997 |
| GB | 2 287 598 A | 9/1995 |
| GB | 2 371 964 A | 8/2002 |

OTHER PUBLICATIONS

U.S. Appl. No. 10/004,363, filed Nov. 1, 2001, Hani-Bashemi and Svatos.

* cited by examiner

Primary Examiner—Kanjibhai Patel
Assistant Examiner—Ali Bayat

(57) ABSTRACT

A method and system for positioning a patient for receiving radiotherapy treatment by performing a computer tomography scan of the patient in a first position to acquire CT data, using the CT data to create one or more images of the patient in the first position, preparing the patient to receive treatment delivery in a second position, acquiring one or more images of the patient in the second position, using a means for comparing the one or more images of the patient in the first position to the one or more images of the patient in the second position, and repositioning the patient until the patient is in substantially the same position as shown in the one or more images of the patient in the first position.

18 Claims, 6 Drawing Sheets

PATIENT POSITIONING BY VIDEO IMAGING

BACKGROUND OF THE INVENTION

Computed Tomography (CT) is a tool used to plan modern radiation therapy. Under direction of an oncologist, a CT device generates multiple x-ray images of a patient and assimilates the images into a two-dimensional cross-sectional CT image of the patient's body. Unlike traditional x-ray images, a CT image depicts both hard objects such as bone and soft tissue including tumors. As a result, the CT image may be used for diagnosis, to delineate diseased tissue and healthy organs-at-risk, to define a treatment isocenter, and to design properties of a radiation beam usable to treat the patient (e.g., beam type, shape, dosage, duration).

CT virtual simulation gives clinicians the flexibility needed to treat the tumor, while avoiding organs-at-risk. This is done by graphic simulation of the treatment process and designing the optimum scenario for the treatment. The use of CT simulation improves the accuracy of treatment planning. More accurate planning puts a heavy demand on accurate patient positioning. In order to create a CT image, the patient is carefully positioned so as to permit x-ray radiation emitted by the CT device to intercept only an area of the patient's body that is of interest, and to avoid tissue in other areas. Immobilization devices and radiation shields are often used to achieve these ends.

Laser projectors provide one method of marking of the patient. The marks placed on patient skin are then used for the placement of patient under the dose delivery system. Laser making relies on a few points for patient alignment. The alignment of these few points ensures the correct placement of the patient as a whole; however, this technique fails to account for body deformations that often occur during transport of the patient. This problem often occurs during treatment of obese patients, and also for the treatment of the breast. For example, it is important to reposition the patient in such a way that a compliant breast is the exact shape as it was while the patient was on the CT table.

Treatment plans are designed to maximize radiation delivered to a target while minimizing radiation delivered to healthy tissue. However, a treatment plan is designed assuming that relevant portions of a patient will be in a particular position during treatment. If the relevant portions are not positioned exactly as required by the treatment plan, the goals of maximizing target radiation and minimizing healthy tissue radiation may not be achieved. More specifically, errors in positioning the patient can cause the delivery of low radiation doses to tumors and high radiation doses to sensitive healthy tissue. The potential for misdelivery increases with increased positioning errors.

SUMMARY OF THE INVENTION

A method and system for positioning a patient for receiving radiotherapy treatment by performing a computer tomography scan of the patient in a first position to acquire CT data, using the CT data to create one or more images of the patient in the first position, preparing the patient to receive treatment delivery in a second position, acquiring one or more images of the patient in the second position, using a means for comparing the one or more images of the patient in the first position to the one or more images of the patient in the second position, and repositioning the patient until the patient is in substantially the same position as shown in the one or more images of the patient in the first position.

The above is a brief description of the present invention. Other features and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
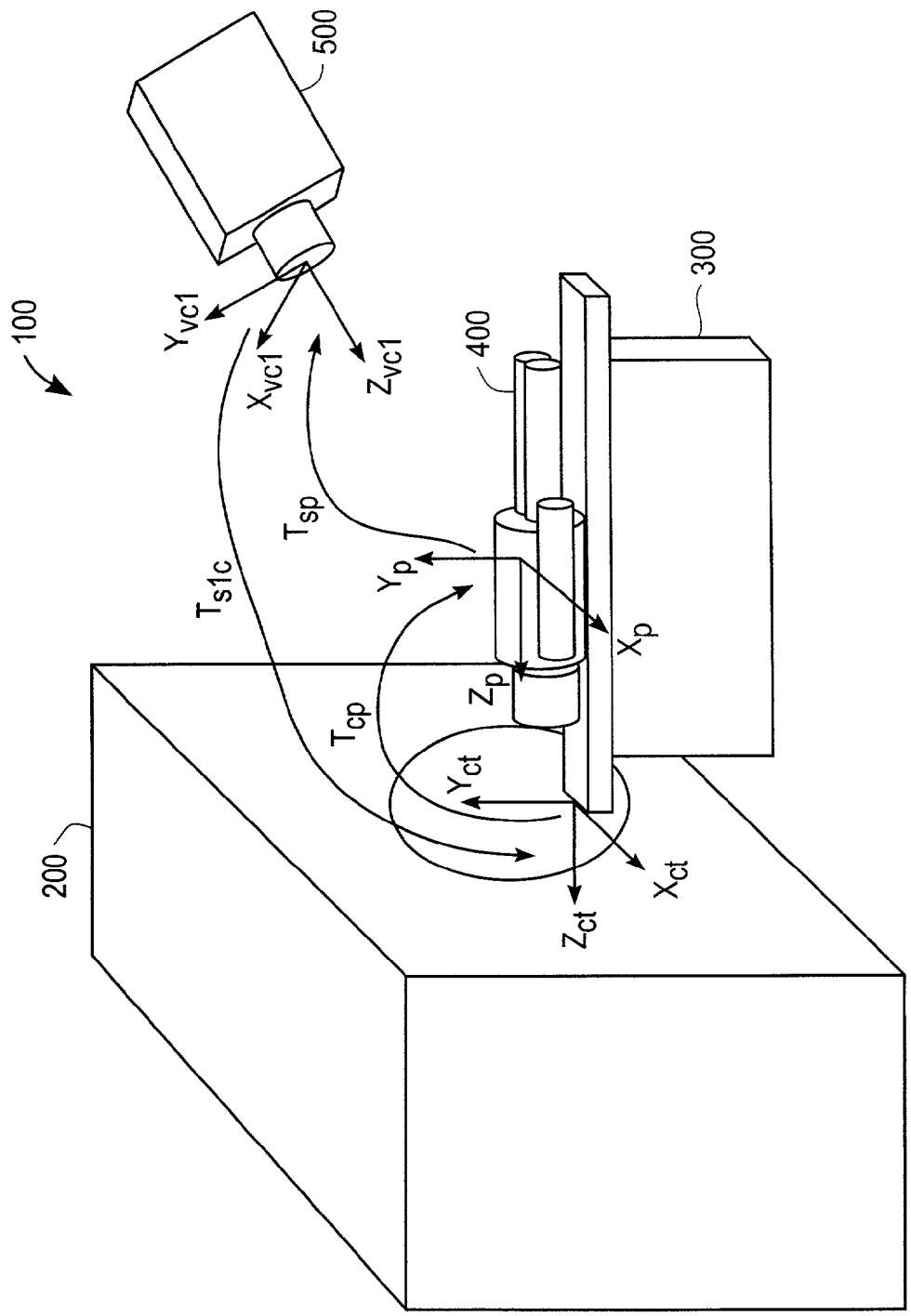
FIG. 1 is a diagram illustrating a CT room according to some embodiments of the present invention and a patient positioned for a CT scan.

Turning now to the drawings, FIG. 1 illustrates computed tomography ("CT") room 100 configured to acquire data in accordance with some embodiments of the present invention. CT room 100 includes CT device 200, CT table 300, patient 400, and virtual camera 500. CT device 200 is used to obtain CT data representing at least a portion of patient 400. Specifically, CT device acquires CT data by exploiting the x-ray principal: as x-rays pass through the body they are absorbed or attenuated at differing levels, thereby creating a matrix or profile of x-ray beams of different strength. In conventional x-ray imaging, an image of the profile is produced using film that is sensitive to x-rays. In the case of CT, the film is replaced by a banana-shaped detector that measures the x-ray profile and outputs data representing the profile.

The detector is mounted on a rotating frame inside CT device 200. Mounted opposite to the detector is an x-ray tube that emits a fan beam of x-rays as the rotating frame spins the x-ray tube and detector around patient 400. As the x-ray tube and detector spin, the detector measures profiles of the attenuated x-ray beam. Typically, in one 360° spin, about 1,000 profiles are measured. Each profile is subdivided spatially by the detector and fed into about 700 individual data channels. Each profile is then reconstructed into a two-dimensional image of the portion or "slice" that was scanned. The two-dimensional images may be processed to create a three-dimensional image. Both the two-dimensional images and the three-dimensional image are referred to herein as CT data, and both show tissue as well as bone. In some embodiments, the acquired CT data are represented in a CT coordinate frame, depicted by $f_{ct}:(x_{ct}, y_{ct}, z_{ct})$ of FIG. 1.

CT table 300 is used to position a patient before, during and after acquisition of CT data. As such, CT table 300 is capable of moving so as to place relevant portions of the patient 400 in the path of the x-ray beam within CT device 200. This movement may be under the control of an operator and/or a computer program. It should be noted that any currently or hereafter-known CT table and CT device may be used in accordance with the present invention.

Figure 2:
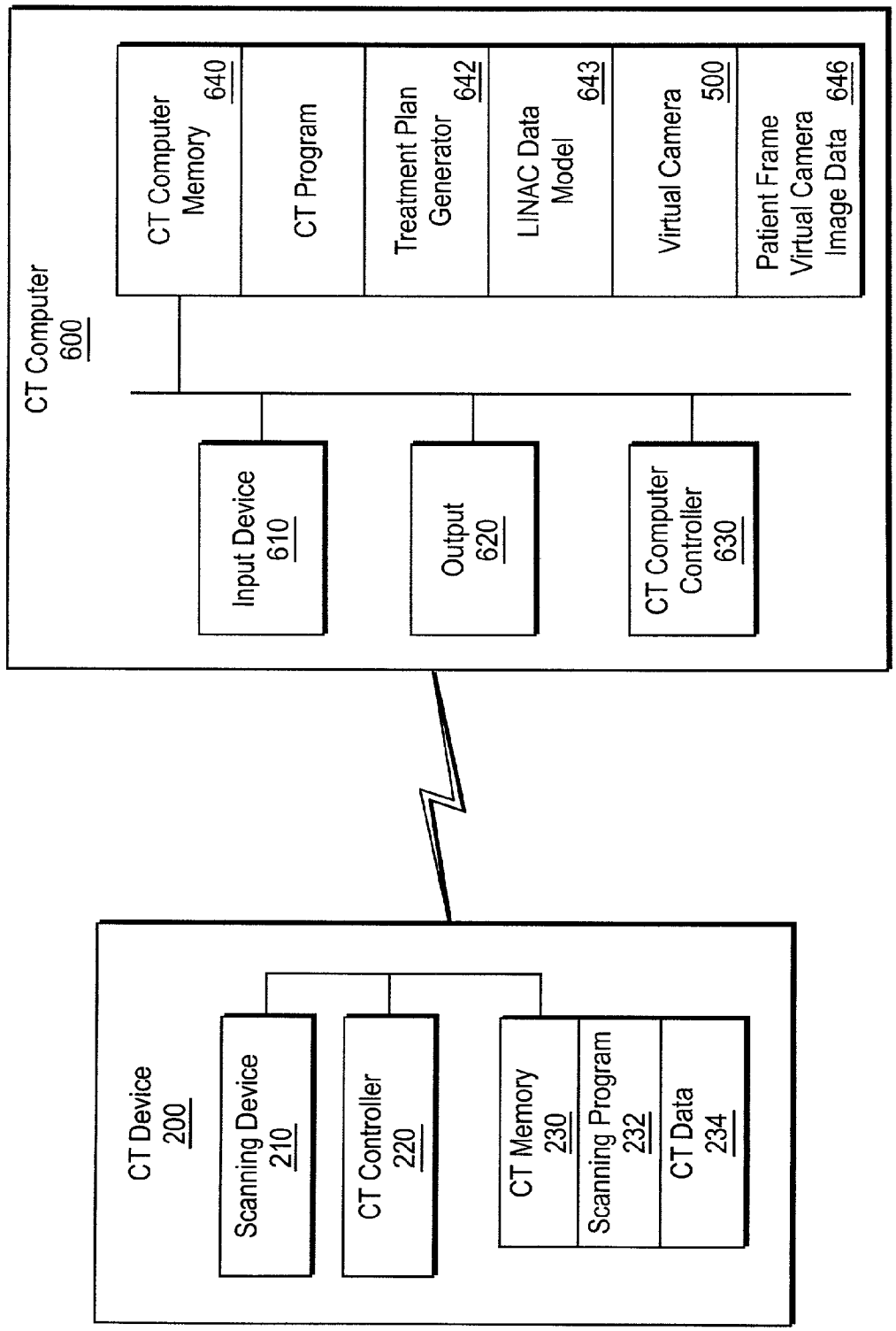
FIG. 2 is a block diagram illustrating elements of devices according to some embodiments of the present invention.

FIG. 2 illustrates internal architectures of various elements of CT room 100, including CT device 200 and virtual camera 500. Also illustrated is an internal architecture of CT computer 600, which is not shown in CT room 100. CT computer 600 may be operated so as to cause CT device 200 to perform steps in accordance with embodiments of the present invention. CT computer 600 may be located within CT room 100, in a radiation-proof room adjacent to CT room 100, or elsewhere.

As shown, CT device 200 includes scanning device 210, which includes the x-ray tube and detector described above as well as other physical devices needed to generate x-ray profiles. CT controller 220 controls scanning device 210 using internal logic and/or executable process steps. Accordingly, scanning device 210 may comprise a microprocessor, a programmable logic controller or the like. Some of these process steps may be part of scanning program 232 stored in memory 230. In this regard, scanning program 232 includes executable process steps for controlling the hardware elements of CT device 100 to scan a body and to thereby generate x-ray profiles. The generated x-ray profiles are stored in memory 230 as CT data 234. CT data 234 may include raw profile data, two-dimensional images generated based on raw profile data, and three-dimensional images generated based on raw profile data and/or two-dimensional images.

CT computer 600 includes input device 610, output device 620, CT computer controller 630, and CT computer memory 640. Input device 610 may be manipulated by an operator to submit commands to CT computer 600 and to CT device 200. Input device 610 may therefore comprise one or more of a keyboard, a pointing device, a touch screen or any other input device. Output device 630 is used to output images, data and text to the operator, and therefore may comprise a display, a printer, and the like. Data may also be input to and output from CT computer 600 using a communication port (not shown) that links CT computer 600 to other devices. For example, commands may be transmitted to and CT data may be received from CT device 200 over such a communication port.

CT computer controller 630 controls elements of CT computer 600 according to internal logic and/or executable process steps. The process steps may be received from another device or stored in memory 640. Process steps used to control the functions of CT device 200 are found in CT program 641. Treatment plan generator stores process steps that are executable to generate a radiation treatment plan based on CT data, virtual camera images, and data of the linear accelerator (linac) data model 643.

CT computer data 644 includes CT data 234 generated by CT device 200 in any format, including raw and/or image format. The virtual camera uses CT data 234 to create a virtual camera image that is in the virtual camera coordinate frame. The virtual camera image is transformed to the coordinate system of the patient, and stored in patient-frame virtual camera image 646. The depiction of virtual camera 500 is FIG. 1 is merely a representation of where an actual camera would be located to acquire the equivalent images of the patient during CT.

Each of the devices shown in FIG. 2 may include less or more elements than those shown. Moreover, transformation and storage of acquired data may be performed by any one or more of the devices. In addition, embodiments of the invention are not limited to the two devices shown.

Figure 3:
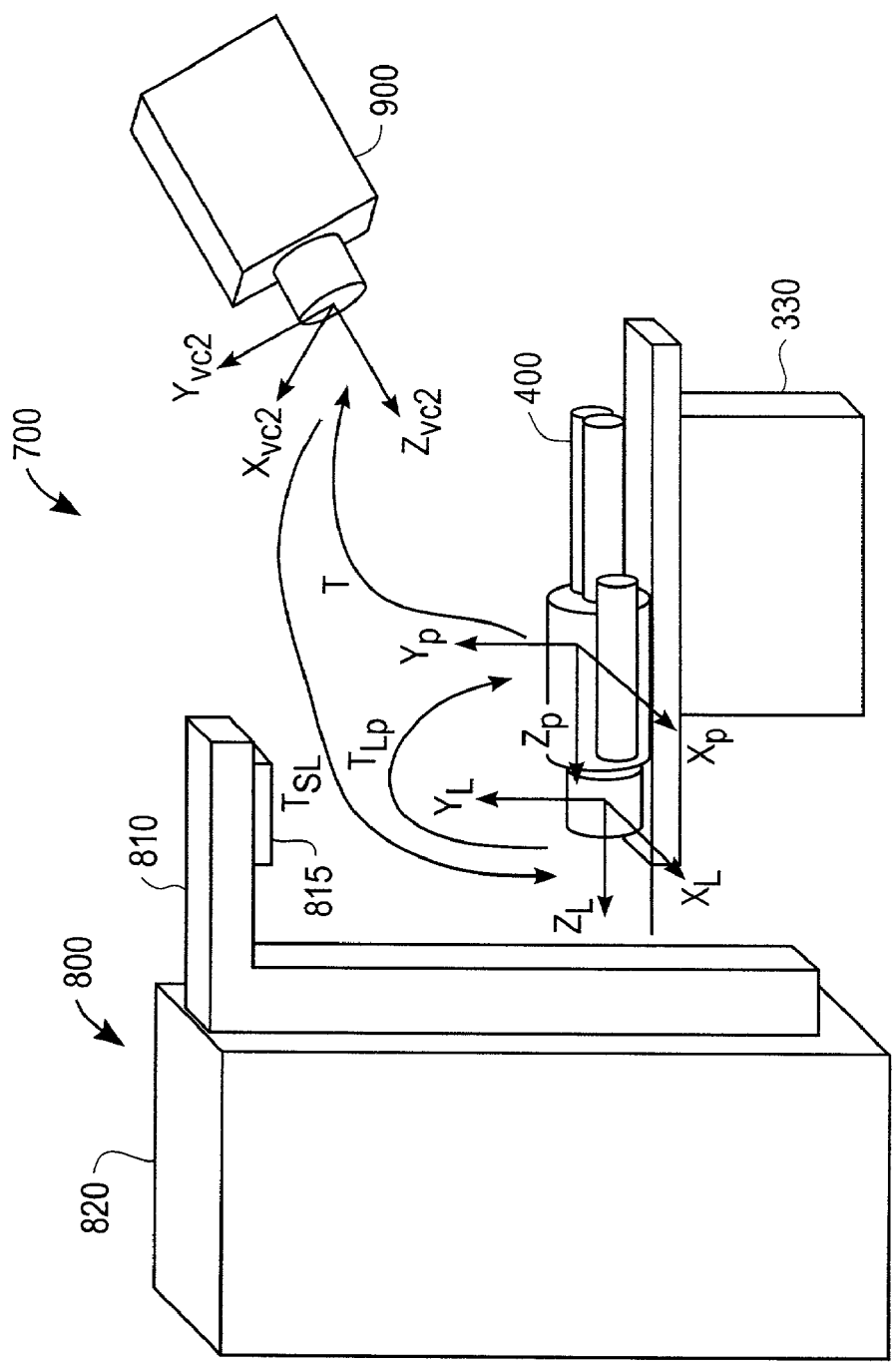
FIG. 3 is a diagram illustrating a radiation treatment room according to some embodiments of the present invention.

For radiation therapy, the patient is moved to a room containing the linac device 300 and positioned on a table. In FIG. 3, a radiation treatment device (linac) is shown and generally indicated at 800. The linac 800 includes a beam shielding device (not shown) within a treatment head 815, a base 820, and a table 830. The radiation treatment device further includes a gantry 810 which can be swiveled about a horizontal axis in the course of a therapeutic treatment. The treatment head 815 is fixed to the gantry 810 for movement therewith and a linear accelerator, located within the gantry, generates high powered radiation. Electron, photon, or any other detectable radiation may be used for the therapy. During treatment, the radiation beam is focused on the patient 400. The zone to be treated is located at the linac isocenter defined by the intersection of the rotational axis of the gantry 810 and the radiation beam axis (the intersection of axes $x_1$, $y_1$ and $z_1$). Accordingly, patient 400 is preferably positioned so that the center of an area to be radiated, or the patient isocenter (located at the intersection of axes $x_p$, $y_p$ and $z_p$), is located at the linac isocenter. The rotatable gantry 810 allows for different beam angles and radiation distributions without having to move the patient.

Figure 4:
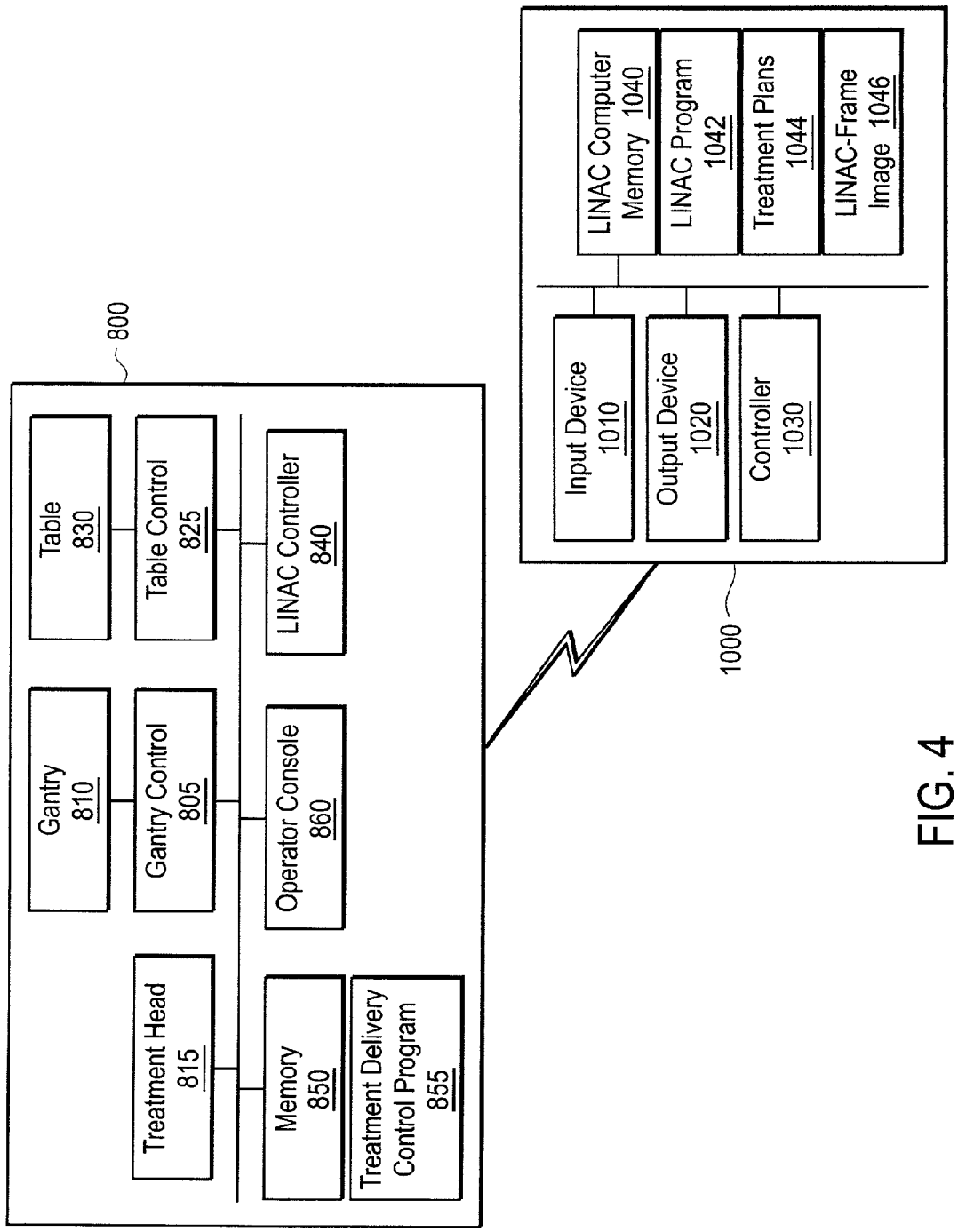
FIG. 4 is a diagram illustrating elements of devices according to some embodiments of the present invention.

Referring now to FIG. 4, a block diagram is shown depicting portions of linac 800, video camera 900 and linac computer 1000. The video camera 900 has a known position and orientation with respect to the gantry 810. The video camera 900 generates images of the patient 400 in position to receive radiation therapy. The images may be shown in real-time. One of ordinary skill in the art would understand that any image-capturing device may be used instead of a video camera. The video camera 900 may be attached to the gantry 810 so that the patient 400 may be viewed from multiple directions by moving the gantry 810. Linac computer 1000 is not shown in FIG. 3 because linac computer 1000 is typically operated by a therapist who is located in a different room so as to be protected from radiation. The therapist operates linac computer 1000 by using input device 1010, such as a keyboard or the like. Data can be input from other devices such as CT computer 600 via an I/O port (not shown). Various data can be output to the therapist before and during treatment via output device 1020.

Linac computer memory 1040 stores data for controlling and generated by linac 800. This data includes process steps of linac program 1042 which are executed by controller 1030 to provide control over linac 800 so as to execute one of treatment plans 1044 defined by an oncologist for a particular patient. One or more of treatment plans 1044 may be generated by CT computer 600 using treatment plan generator 642 and transmitted to linac computer 1000 via any type of communication link usable to transmit data. Treatment plans 1044 may be generated by linac computer 1000 using linac program 1042.

In this regard, the functions described herein as being performed by CT computer 600 and linac computer 1000 may be performed by a single device or by other devices including CT device 200, virtual camera 500, linac 800 and video camera 900. Those skilled in the art will also appreciate that any suitable general purpose or specially programmed computer may be used to achieve the functionality described herein.

Video camera 900 acquires an image of a portion of a patient's body while the patient is in a position substantially maintained in preparation for radiation treatment. This image is used to determine whether the position corresponds to a position maintained by the patient during acquisition of CT data. Anatomical structure coordinates are represented in terms of the linac coordinate system to ensure that radiation is delivered to the intended target.

Figure 5A:
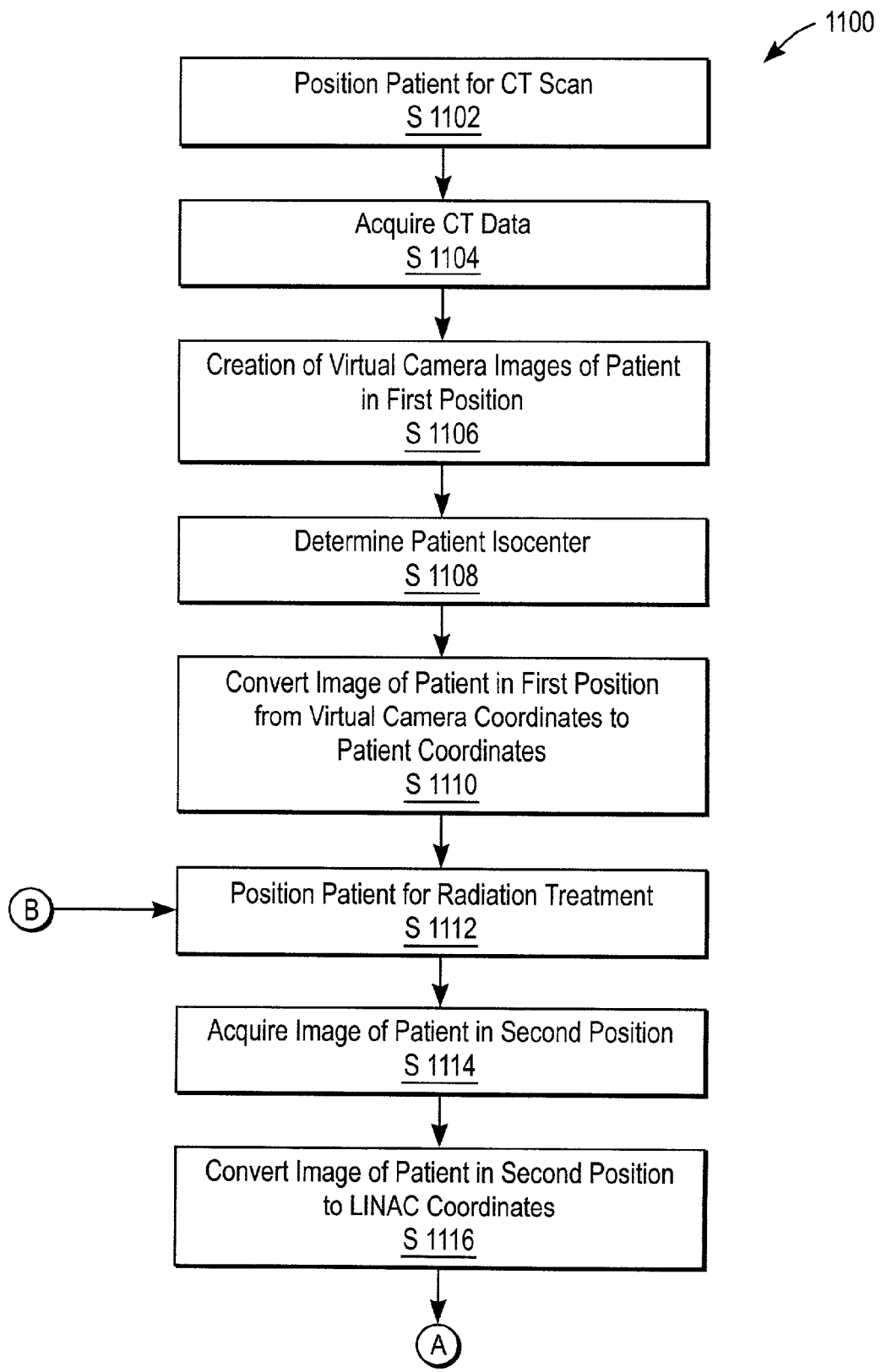
FIGS. 5a–5b are flow diagrams illustrating process steps according to some embodiments of the present invention.
Figure 5B:
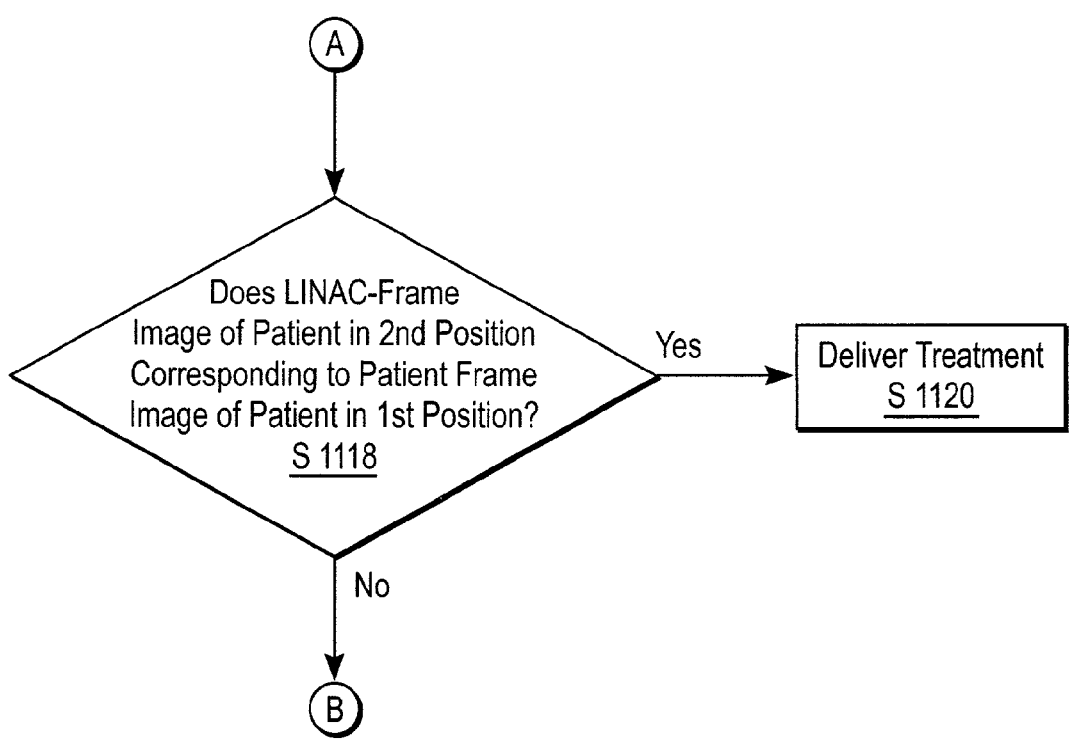

FIGS. 5a and 5b illustrate process steps 1100 according to some embodiments of the present invention. Process steps 1100 may be performed by various devices under the control of controller-executable process steps stored locally to the devices or received from other devices. Embodiments of the present invention may differ from the description. The particular arrangement of process steps 1100 are not meant to imply a fixed order to the steps; embodiments of the present invention can be practiced in any order that is practicable.

Briefly, process steps 1100 execute to acquire a first virtual camera image of at least a portion of a patient's body while the patient is in a first position, and to acquire a second image representing the patient's body while the patient is in the second position.

In step S1102, a patient is positioned for a CT scan in CT room 100. The patient's body is positioned on CT table 300 to be scanned. During the scan, CT device 200 acquires CT data in step S1103. The acquired CT data is stored among CT data 234 and CT computer data 644, and the CT data are represented in the CT coordinate frame.

The coordinate system of a virtual camera 500 located in the CT room 100 is defined by $f:(x_{vc1}, y_{vc1}$ and $z_{vc1})$ The virtual camera 500 may move anywhere with respect to the CT machine. In step S1106, virtual camera images of the patient are created from the CT data 234. The virtual camera images may be generated from any point in space, and are represented in the virtual camera coordinate system.

The virtual camera images are based on the extracted skin information and the imaging model of the virtual camera. The skin surface may be extracted from the CT data 234 and rendered in three dimensions. The three-dimensional surface is intended to substantially mimic a surface of the patient's body and other physical elements as positioned during acquisition of the CT data 234. 3D Surface Shaded Display (SSD) of the skin surface may be created with the following considerations: (1) The geometric model of a virtual camera, namely, center of projection (viewpoint), lens parameters (focal lens, aperture, depth of focus, distortion, etc.), view angle, i.e. optical axis of the camera, and magnification or field-of-view; (2) lighting model: the number of light sources, direction of light, and position of each light source; (3) surface properties: color, diffuseness, and specularity.

Next, a patient isocenter is determined in step S1108. The patient isocenter is selected from the CT data 234. The patient isocenter is a point within the patient's body on which a radiation beam should be focused according to a treatment plan. Accordingly, a position of the patient isocenter is determined by a specialist who examines graphic representations of the CT data 234 acquired in step S1104. The representations may be displayed by output device 620 and/or may be presented by output device 620 in hardcopy form.

The patient coordinate system $f_p:(x_p, y_p, z_p)$ is centered at the patient isocenter. The patient isocenter may be marked on the patient by tattoos, an immobilization structure, or other methods known to those of ordinary skill in the art. The patient isocenter is located at the intersection of axes $x_p$, $y_p$ and $z_p$ of FIGS. 1 and 3. Using the patient isocenter with respect to the patient coordinate frame, the virtual camera image data is converted in step S1110 to the patient coordinate frame. The conversion may be performed by CT computer 600, and the converted data may be stored among patient-frame image data 646. The transformation matrix $T_{sp}$ transforms the images created by the virtual camera from 500 the virtual camera coordinates to the patient coordinate system.

The patient is positioned to receive radiotherapy treatment in step S1112. In step S1110, video camera 900 acquires a video camera image representing at least the same portion of the patient's body as depicted in the virtual camera image from the CT data 234. The acquired video camera image is represented in the video camera coordinate frame $x_{vc2}$, $y_{vc2}$ and $z_{vc2}$. Next, in step S1116, linac computer 1000 converts the video camera image acquired in step S1114 to the linac coordinate frame using transformation matrix $T_{sl}$. $T_{sl}$ defines the transformation between the video camera coordinate system and the linac coordinate system. The converted data is stored among Linac-frame surface data 1046 of linac computer memory 1040.

In step S1118, Linac computer 1000 executes Linac program 1042 to determine if the video camera image from step S1116 corresponds to the virtual camera image produced in step S1106. Patient alignment is achieved when the patient isocenter is placed at the linac isocenter. Once the patient isocenter is aligned with the linac isocenter, the position of the video camera 900 may be given with respect to the patient isocenter. Thus, if $T_{sp}=T_{sl}$, and $T_{pl}=[I]$ (identity matrix), the video image matches the virtual image and the patient is correctly aligned. The similarity, or lack thereof, between the virtual and the real video images is the basis for deciding if the patient is correctly positioned. The accuracy of positioning depends on the optics set-up. Typically, misalignments on the order of 1 mm may be detected visually, while automatic techniques may detect misalignments on the order of a fraction of millimeter. Rotational misalignments on the order of 1 degree may be detected visually. Automatic techniques my detect rotational misalignments on the order of a fraction of a degree.

Step S1118 may include manual viewing of two superimposed surfaces represented by the two sets of data, automated analysis of the data sets, or any other process.

For example, blending the virtual image with the on-line video stream is one method for matching the two images. A control may be used to adjust this blending. The following formula may be used to determine how the blending factor is used to merge/fuse the two images:

$$I_{out}=fIvc+(1-f)Irc$$

where $f:[0.0,1.0]$, $I_{out}$ is the pixel intensity of output image, $I_{vc}$ is the pixel intensity of the virtual camera image, and $I_{rc}$ is the pixel intensity of the real camera image.

Another method of image comparing the virtual camera image to the video camera real-time image includes, but is not limited to, blinking the screen with alternate images from the virtual camera and the video camera.

CT visible markers may be added to the patient's skin to provide distinct landmarks in the CT rendered virtual images, which may be matched to markers in the real video image. These markers may be aluminum patches that adhere to the patient skin.

If the patient is positioned properly, flow proceeds to step S1120 for delivery of radiation treatment. If the data are determined not to correspond, then the patient isocenter is not located substantially at the linac isocenter, the patient 400 is not properly positioned. Flow therefore moves back to step S1112, where the patient must be repositioned. Repositioning in step S1115 may include any method of changing a position of patient relative to linac treatment head 815, including one or more of instructing patient 400 to move, physically moving patient 400, rotating gantry 810, and moving linac table 830. Patient 400 may be repositioned automatically by linac controller 800 or linac computer 1000 based on analyzed differences between the linac-frame video camera image and the patient-frame virtual camera image, and/or manually by an operator using operator console 860 or input device 1010. The operator may be guided by instructions determined based on the analyzed differences and presented through console 860 or output device 1020. In some embodiments, the operator is presented with an image representing the virtual camera image superimposed on a video camera on-line image.

The real-time video images obtained in the linac room may be automatically registered with the virtual camera images generated from the CT data 234. In this case, the computer compares the real-time image sequence with the virtual camera image and determines the patient movement needed to match the two images.

In an alternate embodiment (not shown), two video cameras are used to give the user three-dimensional perception. The distance between the two cameras will be such that gazing at the object provides 6–7 degree angle between the two cameras. (similar to the human visual system gazing at an object about 40 cm away). The pair of images generated from the left and right cameras are displayed on a stereo monitor as the left and right images, respectively. The user wears stereo goggles synchronized with the left and right images of the screen, i.e. the right eye sees only the right video image and the left eye sees only the left video image. This gives the user 3D stereo perception.

The virtual images of the patient surface corresponding to the right and the left eye will be generated from the CT data 234 and viewed on the stereo monitor (in the linac room). This provides two pairs of stereo images; one coming real-time from the patient, and the other static virtual stereo image generated from the CT data. The patient's position will be changed until the two real-time images match the static virtual images.

In some embodiments, features of process steps 1100 may be used to provide gated radiation treatment. Gating involves the acquisition of images only when the patient's body is at a particular position corresponding to a point in a cycle of motion. For example, one gating treatment calls for the acquisition of the CT data at a point after exhalation and just prior to inhalation and the video camera image of the patient is also acquired at the same point in another cycle of breathing.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for positioning a patient for receiving radiotherapy treatment, the method comprising:

performing a computed tomography scan of the patient in a first position to acquire CT data;

using the CT data to create one or more images of the patient in the first position, the one or more images being of the skin surface of the patient;

preparing the patient to receive treatment delivery in a second position;

acquiring one or more images of the patient in the second position;

comparing the one or more images of the patient in the first position to the one or more images of the patient in the second position;

repositioning the patient until the patient is in substantially the same position as shown in the one or more images of the patient in the first position.

2. The method of claim 1 wherein the patient is repositioned to be within 1 mm of the one or more images of the patient in the first position.

3. The method of claim 1 wherein the patient is repositioned to be within 1 degree of the one or more images of the patient in the first position.

4. The method of claim 1 wherein the one or more images of the patient in a second position are real-time video images.

5. The method of claim 1 wherein a gated acquisition device is used such that the image of the patient in the second position is acquired at the same point of a cycle as the image of the patient in the first position.

6. The method of claim 1 wherein the comparing of the image of the patient in the first position to the image of the patient in the second position is performed by blending the video image of the patient in the first position with the corresponding image of the patient in the second position.

7. The meted of claim 1 wherein the comparing of the image of the patient in the first position to the image of the patient in the second position is performed by blinking a display screen and alternating the image of the patient in the first position to the image of the patient in the second position.

8. The method of claim 1 wherein one or more visible markers are added to a surface of the patient to provide landmarks in the image of the patient in the first position to be matched to images of the patient in the second position.

9. The method of claim 1, wherein the one or more images of the patient in the second position comprises a video image captured by a camera.

10. A system for positioning a patient to receive radiotherapy treatment, the system comprising:

a computer tomography machine that generates CT data of the patient in a first position;

a processor capable of generating one or more images of a patient in a first position from the CT data, the one or more images being of the skin surface of the patient;

a memory configured to at least temporarily store the one or more images of a patient in a first position from the CT data;

one or more video cameras located in the area where the patient is to receive radiotherapy treatment said one or more video cameras acquiring one or more images of the patient in a second position;

a means for comparing the one or more images of the patient in the first position to the one or more images of the patient in the second position; and a means for repositioning the patient until the patient is in substantially the same position as illustrated in the one or more images of the patient in the first position.

11. The system of claim 10, wherein two video cameras are placed to create a set of stereo video images of the patient in the second position, and a set of stereo goggles are used which are synchronized with the stereo video images of the patient in the second position which gives three-dimensional stereo perception.

12. A system for positioning a patient to receive radiotherapy treatment, the system comprising:
   a computer tomography machine that generates CT data of the patient in a first position;
   a processor capable of generating one or more images of a patient in a first position from the CT data, the one or more images being of the skin surface of the patient;
   a memory configured to at least temporarily store the one or more images of a patient in a first position from the CT data; one or more video cameras located in the area where the patient is to receive radiotherapy treatment, said video camera acquiring one or more images of the patient in a second position; a means for comparing the one or more images of the patient in the first position to the one or more images of the patient in the second position; and a means for repositioning the patient until the patients is in substantially the same position as illustrated in the one or more images of the patient in the first position.

13. The system of claim 12 wherein two video cameras are placed to create a set of stereo video images of the patient in the second position, and a set of stereo goggles are used which are synchronized with the stereo video images of the patient in the second position which gives three-dimensional stereo perception.

14. A system for positioning a patient to receive radiotherapy treatment, the system comprising:
   one or more video cameras located in the area where the patient is to receive radiotherapy treatment, said one or wore video cameras acquiring one or more images of the patient in a position to receive radiotherapy treatment, the one or more images being of the skin surface of the patient;
   a means for receiving one or images of the patient in a scanning position;
   a means for comparing the one or more images of the patient in the scanning position to the one or more images of the patient in the position to receive radiotherapy treatment; and
   a means for repositioning the patient until the patient is in substantially the same position as illustrated in the one or inure images of the patient in the scanning position.

15. The system of claim 14 further comprising a computer tomography machine that generates CT data of the patient in the scanning position; a processor capable of generating one or more images of a patient in a scanning position from the CT data; and a memory configured to at least temporarily store the one or more images of a patient in a scanning position from the CT data.

16. The system of claim 14, wherein two video cameras are placed to create a set of stereo video images of the patient in the position to receive radiotherapy treatment, and a set of stereo goggles are used which are synchronized with the stereo video images of the patient in the position to receive radiotherapy treatment which gives three-dimensional stereo perception.

17. A method for positioning a patient for receiving radiotherapy treatment, the method comprising:
   performing a computed tomography scan of the patient in a first position to acquire CT data;
   using the CT data to create one or more images of the patient in the first position;
   preparing the patient to receive treatment delivery in a second position;
   acquiring one or more images of the patient in the second position;
   comparing the one or more images of the patient in the first position to the one or more images of the patient in the second position the comparing of the image of the patient in the first position to the image of the patient in the second position is performed by blending the video image of the patient in the first position with the corresponding image of the patient in the second position; and
   repositioning the patient until the patient is in substantially the same position as shown in the one or more images of the patient in the first position.

18. A method for positioning a patient for receiving radiotherapy treatment, the method comprising:
   performing a computed tomography scan of the patient in a first position to acquire CT data;
   using the CT data to create one or more images of the patient in the first position;
   preparing the patient to receive treatment delivery in a second position;
   acquiring one or more images of the patient in the second position;
   comparing the one or more images of the patient in the first position to the one or more images of the patient in the second position, the comparing of the image of the patient in the first position to the image of the patient in the second position is performed by blinking a display screen and alternating the image of the patient in the first position to the image of the patient in the second position; and
   repositioning the patient until the patient is in substantially the same position as shown in the one or more images of the patient in the first position.

* * * * *